United States Patent [19]
Vaccaro

[11] Patent Number: 6,102,950
[45] Date of Patent: Aug. 15, 2000

[54] INTERVERTEBRAL BODY FUSION DEVICE

[76] Inventor: Alex Vaccaro, 925 Chestnut St., 2nd Floor, Philadelphia, Pa. 19107

[21] Appl. No.: 09/232,713

[22] Filed: Jan. 19, 1999

[51] Int. Cl.[7] ........................................................ A61F 2/44
[52] U.S. Cl. ................................................ 623/17; 606/61
[58] Field of Search ................................. 606/60, 61, 68, 606/69, 70, 71; 623/16, 17

[56] References Cited

U.S. PATENT DOCUMENTS

| | | |
|---|---|---|
| 4,401,112 | 8/1983 | Rezaian . |
| 4,834,757 | 5/1989 | Brantigan .................................. 623/17 |
| 4,863,476 | 9/1989 | Shepperd .................................. 623/17 |
| 5,015,247 | 5/1991 | Michelson ................................. 606/61 |
| 5,123,926 | 6/1992 | Pisharodi ................................. 623/17 |
| 5,171,278 | 12/1992 | Pisharodi ................................. 623/17 |
| 5,236,460 | 8/1993 | Barber ..................................... 623/17 |
| 5,522,899 | 6/1996 | Michelson ................................. 623/17 |
| 5,554,191 | 9/1996 | Lahille et al. ............................ 623/17 |
| 5,571,190 | 11/1996 | Ulrich et al. ............................. 623/17 |

FOREIGN PATENT DOCUMENTS

| | | |
|---|---|---|
| 0 566 810 A1 | 10/1993 | European Pat. Off. . |
| 2636 227 | 3/1990 | France . |
| 560141 A1 | 9/1993 | Germany . |
| 1560 184 | 7/1988 | U.S.S.R. . |
| WO 94/04100 | 3/1994 | WIPO . |
| WO 95/00082 | 1/1995 | WIPO . |

*Primary Examiner*—Michael Buiz
*Assistant Examiner*—David O. Reip
*Attorney, Agent, or Firm*—Richard C. Litman

[57] ABSTRACT

An intervertebral body fusion device has a wedge body, a cage component with a plurality of deployable spines having end plate penetrating teeth, and a contraction mechanism for drawing the wedge body into the cage component. The device is surgically placed intervertebrally into the spine from an anterior surgical approach. In its final surgically-implanted position, the wedge body is substantially fully drawn within the cage component, resulting in a full deployment of teeth and associated spines into the adjacent end plates of the vertebral bodies, while simultaneously restoring the angle of lordosis to the spine.

20 Claims, 7 Drawing Sheets

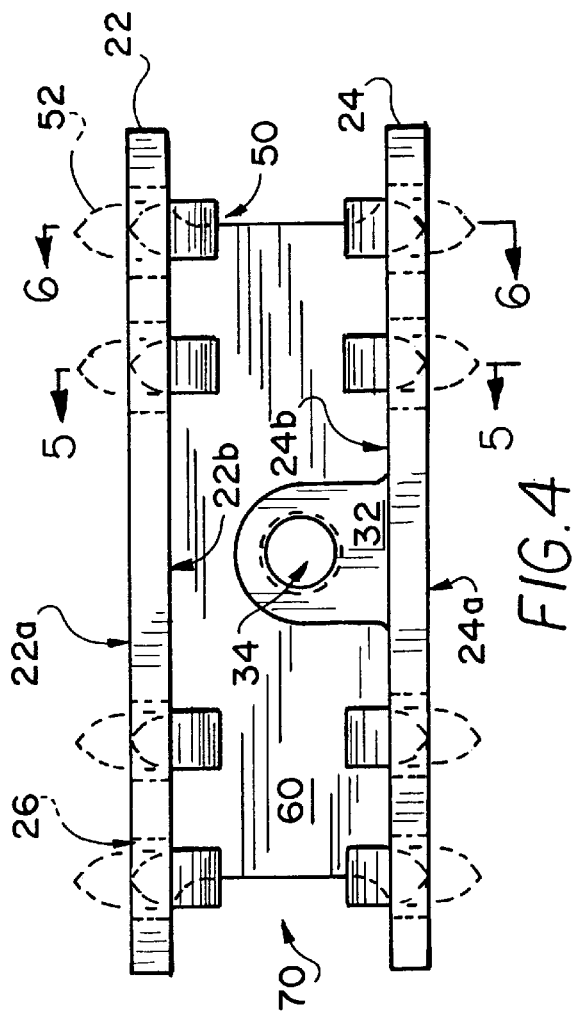
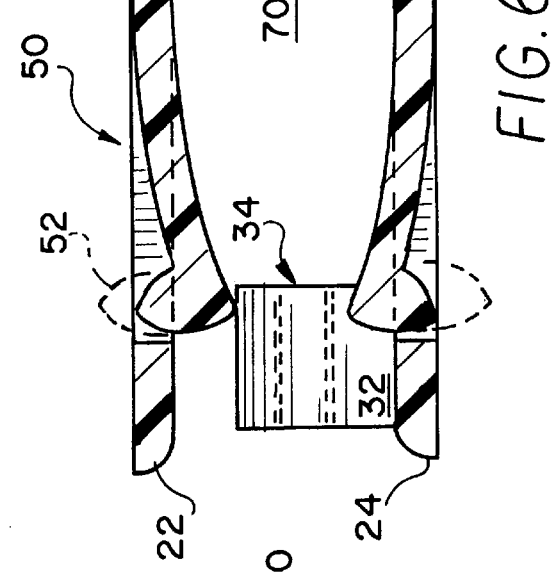
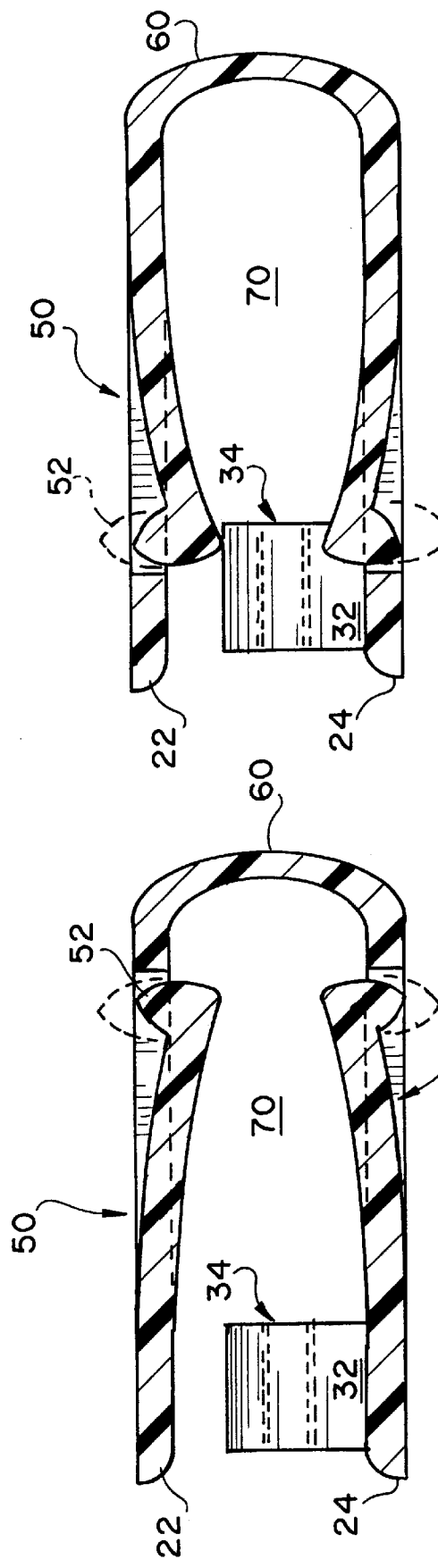

INTERVERTEBRAL BODY FUSION DEVICE

BACKGROUND OF THE INVENTION

1. Field of the Invention

The present invention relates to an intervertebral body device for restoring a proper angle of lordosis to the spine, and, adapted to be inserted from an anterior approach between the vertebral bodies of two vertebrae, particularly during lumbar fusion surgery.

2. Description of the Related Art

A plethora of endoprostheses exist for replacing intervertebral disks after diskectomy or to implement surgical fusion of vertebral bodies. Each such endoprosthesis attempts to restore one or more qualities inherent to the disk or spine by simulating the natural properties of the disk, often by simulating its anatomical structure. Thus, attempts by a single device to restore a plurality of spinal qualities (such as rotation, cushioning, and lordosis) often results in compromise among the several structural features of such device.

However, the critical function of such endoprosthesis is to restore the lordosis angle between corresponding vertebrae, particularly for the purpose of vertebral fusion surgery wherein the device preserves lordosis while a bone graft fuses adjacent vertebrae. The greatest angles of lordosis are typically associated with the lumbar spine, where vertebral bodies have broad, thick, and relatively flat end plates. However unfortunately, the typical related-art endoprosthesis (often referred to as a cage) must be provided in a range of dimensional sizes to suit the anatomy of a patient, which cage then has a fixed dimension. Hence, a practical and simple endoprosthesis is desired which, first, restores lordosis, next, takes particular advantage of the inherent structural integrity and support area of the lumbar vertebral body end plates by providing a broad bearing surface, and further, provides an adjustable angle to that bearing surface. Such device is particularly desirable where lumbo-sacral fusion is indicated, wherein consequent spinal rotation loss results in a relatively lesser post-surgical inconvenience for the patient than that consequent to fusion of other vertebral bodies.

Another consideration of the fusion surgical technique is the amount of distraction necessary to insert and secure any given endoprosthetic device within the intervertebral space. As a general rule, insertion of an endoprosthesis eliminating distraction unnecessary to the restoration of the proper angle of lordosis is beneficial to the healing process. However, to insert, position and secure most of the related-art endoprostheses, unnecessary distraction is required which, at a minimum, causes displacement of surrounding healthy tissues, often with associated tearing, stretching or other damaging consequences. In the extreme, insertion of such devices requires actual destruction of the surrounding healthy soft and bony tissue. For example, an endoprosthesis having spikes which in order to be properly secured to the vertebral body end plates requires distraction beyond the proper angle of lordosis would unnecessarily affect the surrounding tissues. Thus, an endoprosthetic device is desired which after diskectomy may be inserted, positioned, and secured in the resulting intervertebral space, without unnecessary distraction of the vertebral bodies and surrounding tissues.

A related consideration is the surgical technique used to remove the endoprothesis after intervertebral fusion of the graft healing process is substantially completed. Simply stated, removal of the endoprothesis should be as simple as it is to put in.

Moreover, when considering the choices of surgical approaches towards the spine in order to insert the endoprosthesis (e.g. anterior, lateral or posterior approaches), the logical approach to the intervertebral gap correlates with an anterior approach. When the lumbar spine is viewed, the gap between vertebral bodies is widest anteriorly, and decreases posteriorly, thus defining the lordosis angle. To best take advantage of both the structural integrity of the vertebral end plates and eliminate unnecessary distraction, the anterior approach is preferred. Thus, an endoprosthesis suitable for use in an anterior approach is desired.

In light of the above considerations, the related art devices fail to teach structures consistent with the functions and purposes of the present invention.

A first group of devices include plates having fixed spikes used to penetrate the vertebral body end plates and secure the device after positioning, but which, due to the fixed relationships of the spikes and plates, require unnecessary distraction to properly engage the spikes. World Organization publication No. 95/00082 published Jan. 5, 1995 describes disk-simulative device having two plates, including fixed spikes, sandwiching a resilient pad which extends across the most of the area between both plates. U.S. Pat. No. 5,571,190 issued Nov. 5, 1996 to Ulrich et al. describes a plurality of cylindrical body segments used in conjunction with a supporting pin of dedicated length passing through a supporting groove for the entire length of the body segments. Each body segment has a toothed crown, which when engaging each other prevents rotation of body segments relative to one another. In order to insert the pin, the vertebrae must be distracted.

A subgroup of such devices are compromised by virtue of additional structures which permit angular motion about a bearing surface. Derwent abstract of European Patent No. 560141-A1 published Sep. 15, 1993 describes a pair of plates having fixed spikes sandwiching a convexly shaped core coacting with the plates to permit rotary motion about a vertical axis, generally collinear with rotation of the spine. WIPO Patent No. 94/04100 published Mar. 3, 1994 describes two plates having fixed spikes, each plate positioned on a centrally positioned ball joint, the joint surrounded by an elastic ring which matches the prosthesis to the physiological lordosis of the vertebral column.

In contrast, European Patent No. 566 810 A1 published Oct. 27, 1992 describes a pair of plates, without vertebral body engaging spikes, sandwiching a resilient pillar of the proper lordotic angle, which is insertable from one end of the plates along a track formed by a pair of channels and fixed in place by a snap closure. Although this configuration permits lateral insertion of the pillar of a dedicated height and angle to restore lordosis, the spikes are sacrificed unless otherwise committing to unnecessary distraction of the vertebrae.

Other devices form a pier between vertebral bodies and telescopingly engage the vertebral body end plates, thus utilizing different operational and structural principals than those employed by the present invention to engage the vertebral end plates. For example, Derwent abstract of French publication No. 2636-227A published Mar. 3, 1990 describes two, spiked-end cylinders connected by a rod passing through a bushing cylinder. Derwent abstract of Soviet publication No. 1560-184A published Apr. 30, 1990 describes a shafted head and a receiving cup for receiving the shaft, the cup and head each having fixed spikes, between which a resilient annular cushion forms a shock absorber. U.S. Pat. No. 5,236,460 issued Aug. 17, 1993 to Barber describes tubular inner and outer bodies which bear platforms having fixed pins, the tubular bodies telescoping relative to one another and having a port for receiving a fluid resin. The injected resin hydraulically forces the telescoping action, and subsequently hardens to set the relative positions of the bodies. U.S. Pat. No. 4,401,112 issued Aug. 30, 1983 to Rezaian essentially describes a screw jack-post positioned between the vertebral body end plates, with an anterior flanking plate for securing the device to the vertebral bodies.

Other various methods and devices have been proposed which attempt to cause expansion within the intervertebral space after diskectomy, each substantially unlike the present invention. U.S. Pat. No. 5,171,278 issued Dec. 15, 1992 to Pisharodi describes a method in which an apparatus uncoils sheets encapsulating a screw which increases only the center diameter of the apparatus as the screw is turned. Inadequate structure is presented to appreciate enablement of the mechanics of such a device. A second embodiment has two opposing ends which, when drawn together by a screw, causes a foldable shell to uplift from the center and incline to each end. U.S. Pat. No. 5,123,926, also to Pisharodi, describes a silastic sheath in which a plurality of multisized springs are contained, each terminating with a spike. After implantation, the sheath is filled with a volume of fluid to create resiliency.

Other more destructive artificial fusion implants include those which require partial removal of bone tissue from proximate vertebral bodies. U.S. Pat. No. 5,015,247 issued May 14, 1991 to Michelson describes a coring device and threaded cylindrical implant which is inserted into a well drilled into the intervertebral disc and vertebral end plates. Similarly, U.S. Pat. No. 4,834,757 issued May 30, 1989 to Brantigan provides a gauge block seated in a square channel formed in the vertebral bodies.

Notably, consideration is given in U.S. Pat. No. 4,863,476 issued Sep. 5, 1989 to Shepperd to the advantages of minimizing incisions in skin and cartilage tissues during implantation of a spinal implant device. The device employs a camming means internally disposed to a pair of elongated body members, preferably a split cylinder having an internal channel and enlarged chamber, which body members at rest abut one another and, in vivo, are expanded diametrically to engage the vertebral bodies. The camming means is preferably a threaded rod with a cam sleeve which, when the rod is turned, is advanced from the chamber between the body halves, thus expanding the split cylinder. At column 7, lines 15–18, the concept of extending a spike by means of a cam device located on the screw-threaded rod is noted. The Shepperd device is clearly intended as a permanent implant to engage opposing vertebral bodies and permit rocking about the cylindrical axis, but fails to teach how diametric expansion of equal amounts along the length of the cylinder restores the proper angle of lordosis, and at best suggests the generic concept of a deployable spike structure inconsistent with that of the present invention.

Finally, and most notably, the principal of using a posterior approach to position expandable pairs of branches of an intersomatic cage to restore lordosis is noted in U.S. Pat. No. 5,554,191 issued to Lahille et al. Each branch is provided with a toothed surface for engaging the vertebral bodies and an opposing inclined surface, the branches driven apart by retracting a cylindrical spreader between the inclined surfaces. The cylinder advances along a threaded shank which is rotatably fixed in the body and adapted to be turned by an appropriate screwdriver. However, first, it is noted that the teeth are fixed relative to the branches, and thus deploy simultaneously with the branches. Moreover, the major disadvantage to using the branched body as taught in Lahille is that the spreader must be advanced towards the branched body by manipulating the threaded shank from a posterior approach, effectively requiring the surgeon to operate the device through the decreased-size opening of the intervertebral gap, as opposed to an anterior approach which does not restrict maximization of the bearing surface of the device.

Therefore, none of the above inventions and patents, taken either singularly or in combination, is seen to describe the instant invention as claimed. Thus a intervertebral body fusion device solving the aforementioned problems is desired.

SUMMARY OF THE INVENTION

An intervertebral body fusion device is provided which has a wedge body, a cage component with a plurality of deployable spines having end plate penetrating teeth, and a contraction mechanism for drawing the wedge body into the cage component. The device is surgically placed intervertebrally into the spine from an anterior surgical approach. In its final surgically-implanted position, the wedge body is substantially fully drawn within the cage component, resulting in a full deployment of teeth and associated spines into the adjacent end plates of the vertebral bodies, while simultaneously restoring the angle of lordosis to the spine.

Accordingly, it is a principal object of the invention to provide an intervertebral body device for restoring a proper angle of lordosis to the spine.

It is another object of the invention to provide a device suitable for use during intervertebral fusion surgery which eliminates unnecessary distraction of vertebral bodies and associated tissue to permit its insertion and securement.

It is a further object of the invention to provide an intervertebral body device adapted to be inserted from an anterior approach between the vertebral bodies of two vertebrae.

Still another object of the invention is to provide an intervertebral body device which deploys a spine for penetration of the vertebral body end plate simultaneously with setting the proper angle of lordosis between vertebrae.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 4 is an elevational anterior view of the cage component of the intervertebral body fusion device according to the present invention in a resting, pre-insertion state.

FIG. 5 is a cross sectional view of the cage component of the intervertebral body fusion device as shown along line 5—5 of FIG. 4.

FIG. 6 is a cross sectional view of the cage component of the intervertebral body fusion device as shown along line 6—6 of FIG. 4.

Similar reference characters denote corresponding features consistently throughout the attached drawings.

DETAILED DESCRIPTION OF THE PREFERRED EMBODIMENTS

Figure 1:
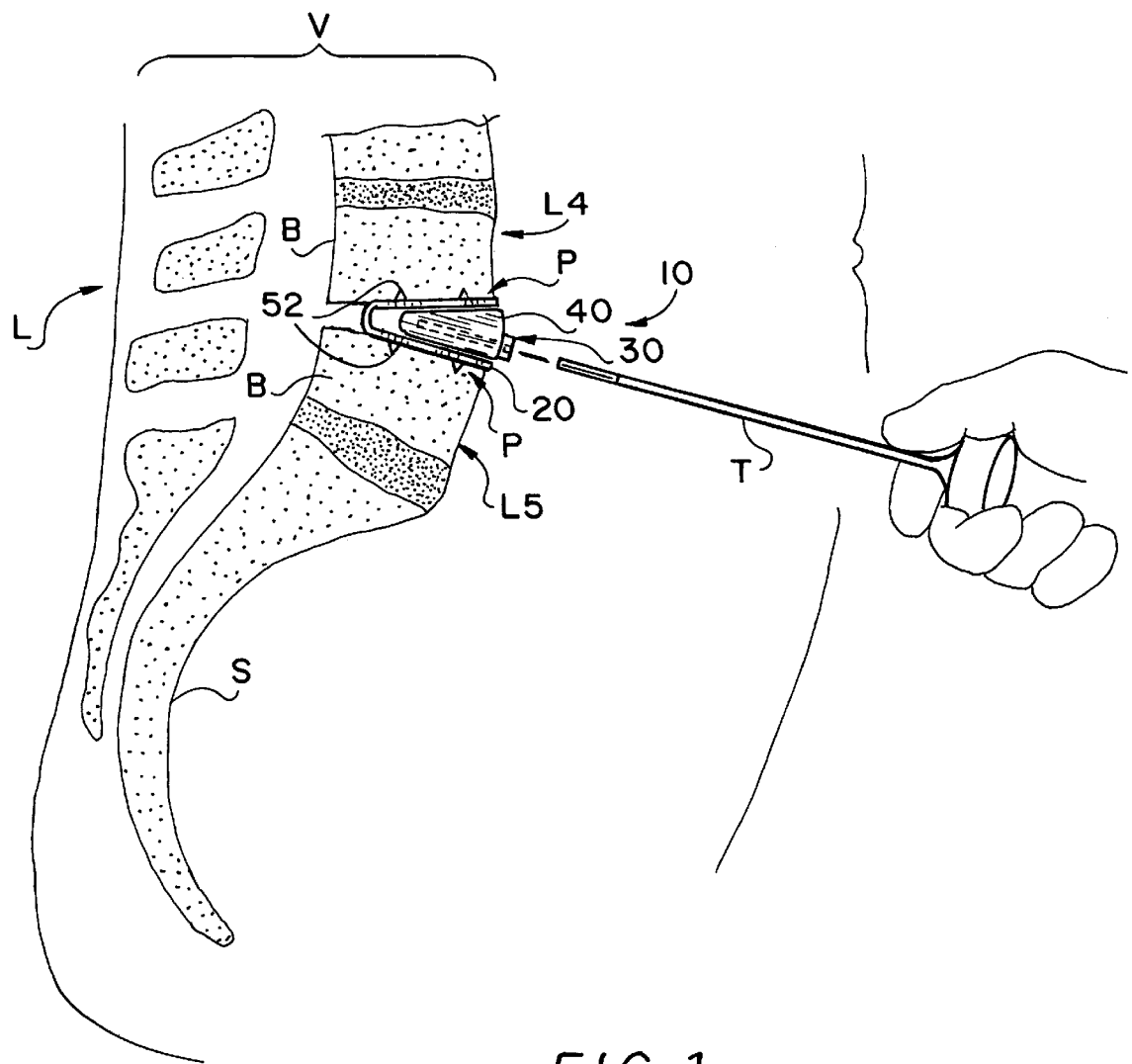
FIG. 1 is an environmental, side view of an intervertebral body fusion device according to the present invention.

As suggested in FIG. 1, the present invention is an intervertebral body fusion device 10 for restoring a proper angle of lordosis to the lumbar spine L, and, adapted to be inserted from an anterior approach A between the vertebral bodies B of two vertebrae V, particularly during lumbar vertebral body fusion surgery. As is more readily observable in FIG. 2, the preferred embodiment 10 of the invention comprises three main structural components, namely, a cage component 20, a wedge body 40, and a contraction mechanism 30 for drawing the wedge body 40 into a nesting relationship within the cage component 20.

The cage component 20 includes a rigid upper member 22 defining a bearing surface 22a and an opposing interior surface 22b, and, a rigid lower member 24 also defining both a bearing surface 24a and an opposing interior surface 24b. Each member 22,24 is preferably a plate, thereby defining each surface as a substantially planar surface. Such a plate is both preferable and suitable for convenient machining of the features of the cage component 20 (as will be further described, namely spines 50 and flexible web 60), as well as, for the advantageous utilization of the large opposing bearing surfaces of the end plates P of adjacent vertebral bodies B during the restoration of lordosis. Such surfaces are particularly prevalent in the lumbar spine L, most particularly between L5 and the os sacrum S.

The lower member 24 is attached to the upper member 22 by a resilient web 60, bridging the upper and lower members 22,24 to define a living hinge. The cage component 20 may be manufactured from a surgical grade material, such as titanium or stainless steel, which provides appropriate material properties to allow tempering to create resilience in the web 60, effectively forming a spring hinging the upper and lower members 22,24 together. As noted, the use of metal plate permits the cage component 10 to be integrally formed to include the web 60 and upper and lower members 22,24. The web 60 also spaces the members 22,24 from one another thereby defining a gap 70 of a predetermined distance for receiving the wedge body 40.

Figure 2:
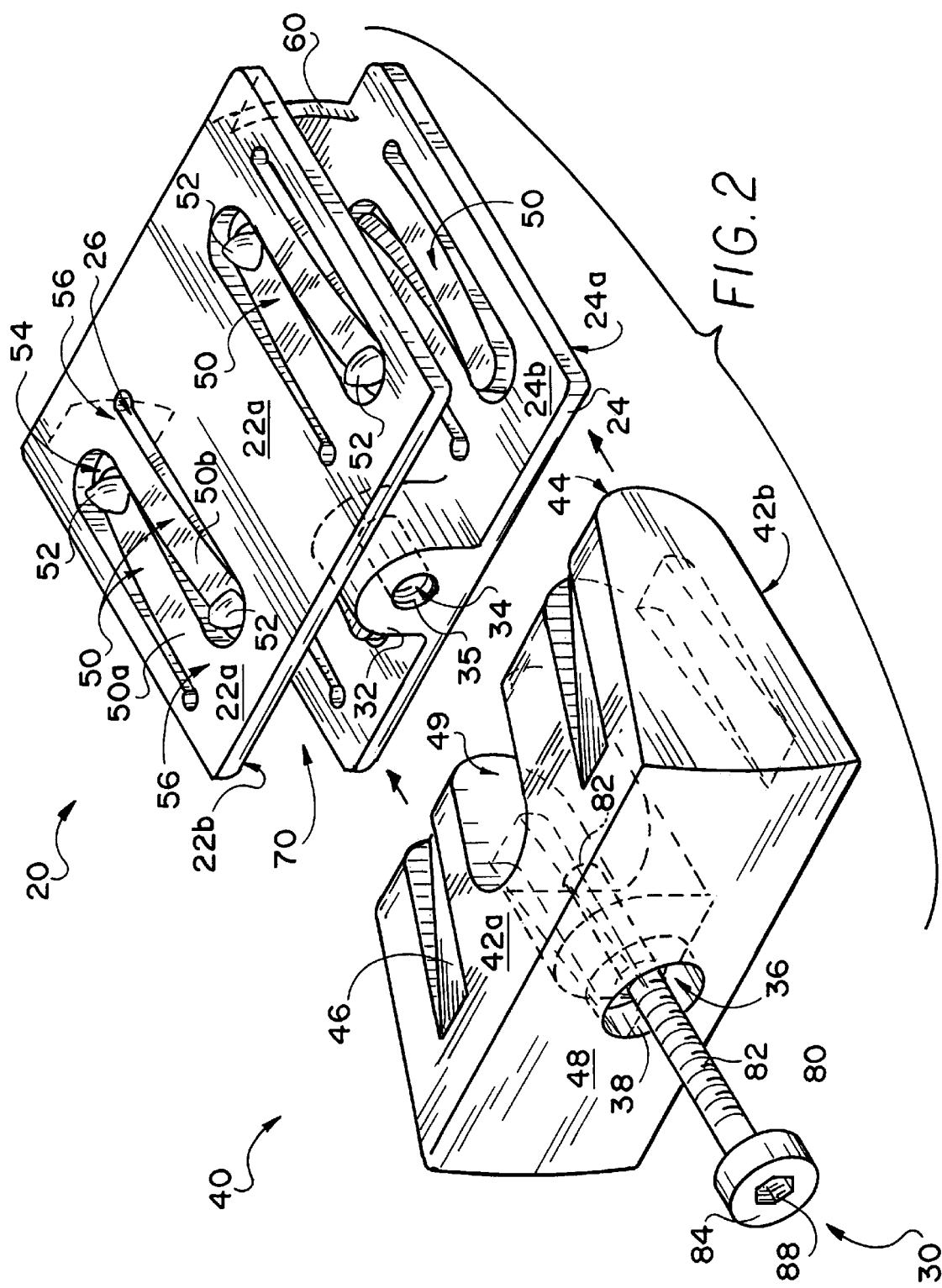
FIG. 2 is an exploded, perspective anterior view of the intervertebral body fusion device according to the present invention.
Figure 7:
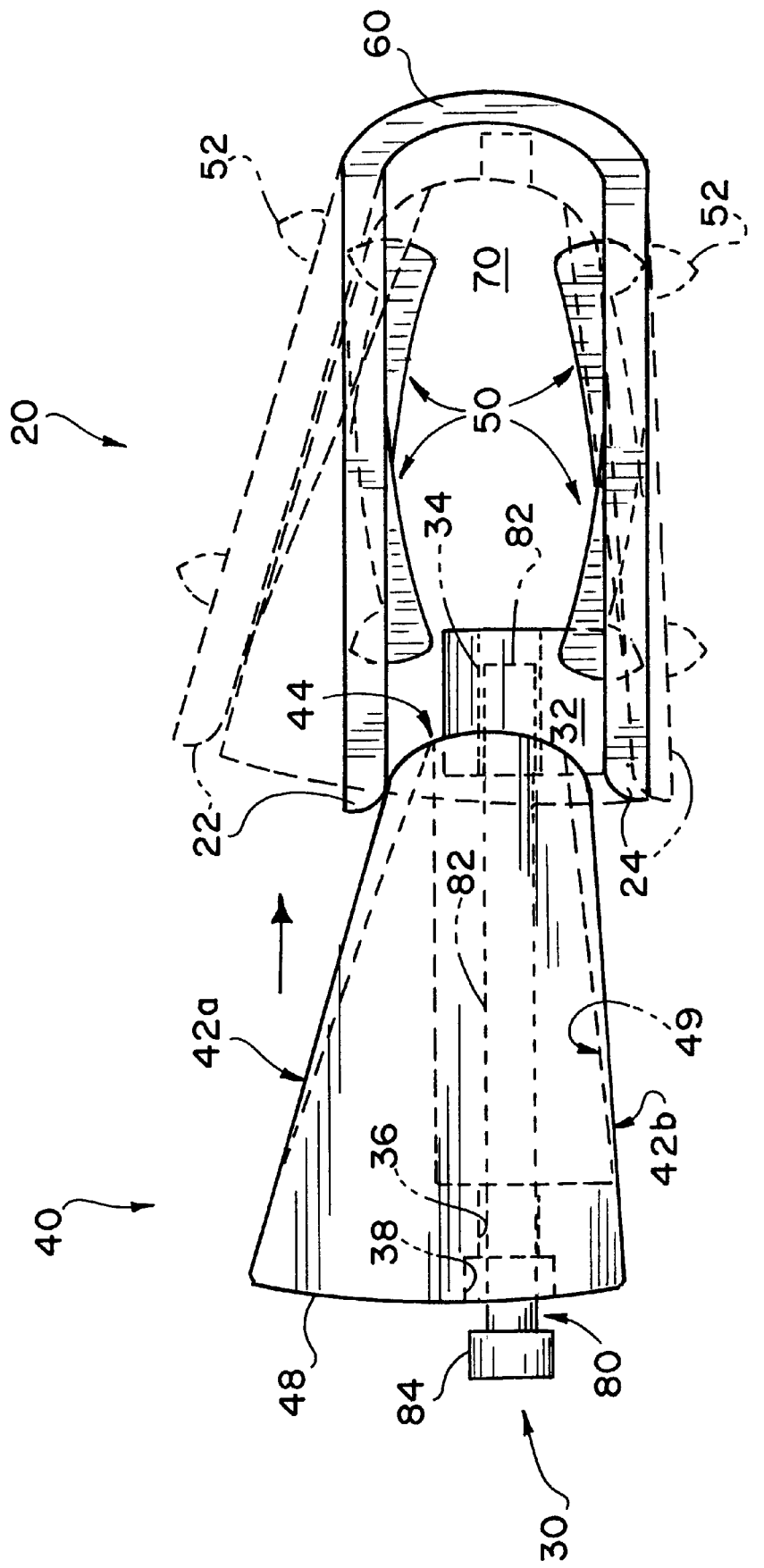
FIG. 7 is a elevational lateral view of the cage and wedge components in coacting positions, representing a pre-insertion state in solid lines wherein the wedge component is substantially external to the cage component, and, a post-insertion state shown in phantom lines wherein the wedge component is substantially fully housed within the cage component.

As seen in FIG. 2, the material properties of the plates of upper and lower members 22,24 and web 60 permit a configuration at rest wherein the upper and lower members 22,24 are positioned in a nearly parallel planar relationship to one another. However, as can be appreciated through comparison with FIGS. 1 and 7, when any opposing and outward biasing forces act simultaneously upon the interior surfaces 22b,24b of each of the upper and lower members 22,24 (namely pressure from wedge body 40), the forces are transmitted through the web 60 to change the angle between the upper and lower members 22,24, the angle generally conforming to the predetermined angle of the wedge body 40. If the proper wedge body 40 is chosen, the primary purpose, to provide the spine L with the proper angle of lordosis, may be achieved.

Figure 3:
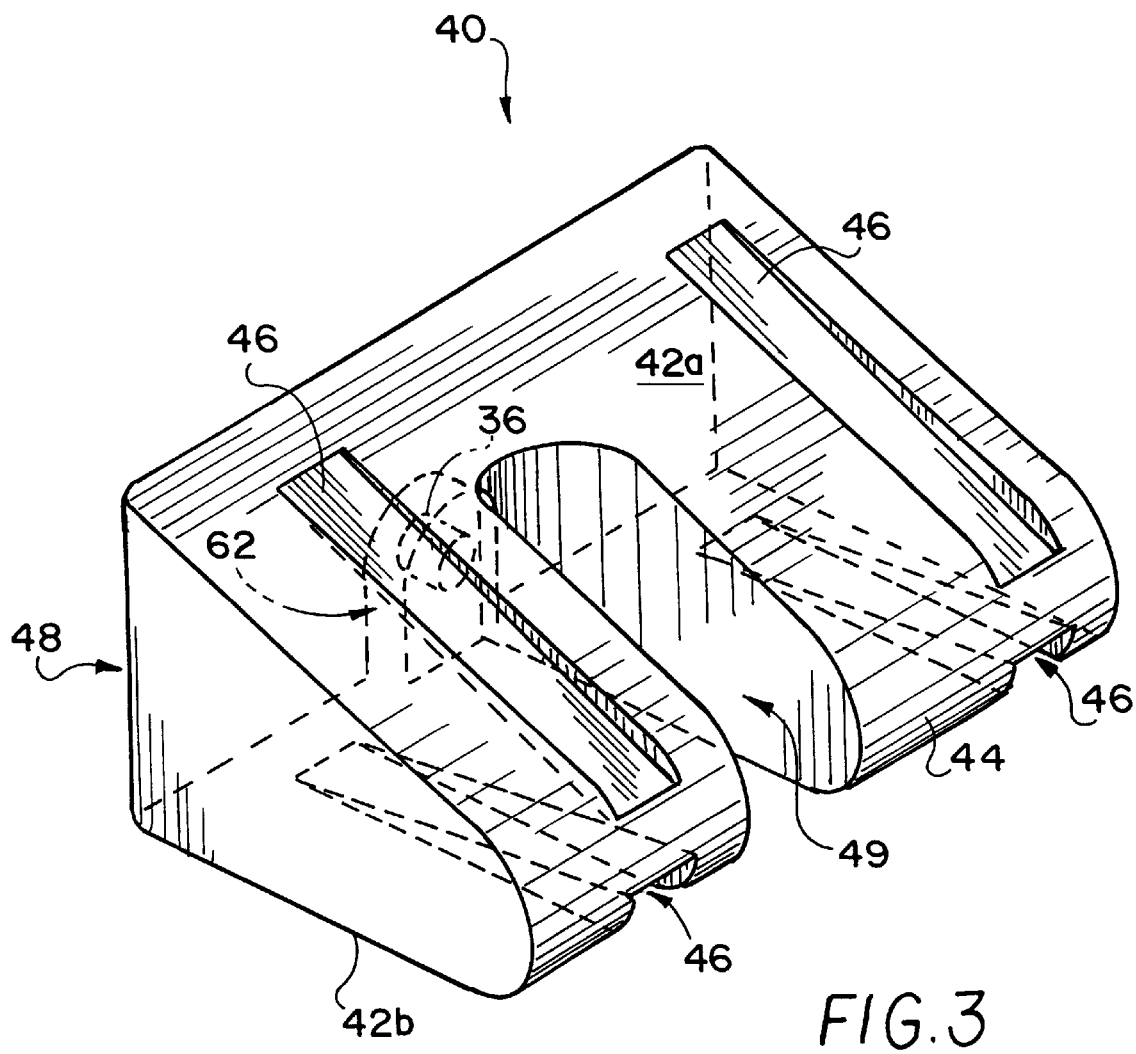
FIG. 3 is a perspective posterior view of a wedge body of the intervertebral body fusion device according to the present invention.

In order to achieve the proper angle, a predetermined range of sizes and wedge angles for each wedge body 50 is provided. As seen in both FIGS. 2 and 3, each wedge body 50 defines a first inclined surface 42a and an opposing second inclined surface 42b, defining a predetermined fixed angle relative to one other. The range of predetermined angles is determined by the range of proper angles of lordosis necessarily desired and found as a result of anatomical variation. Moreover, the wedge body 40 is dimensioned and configured to be received and substantially housed in gap 70. The inclined surfaces 42a,42b meet at a forward face 44 which truncates the apex of the angle, and terminate at a rear face 48. Thus, in the preferred embodiment where upper and lower members 22,24 lie in substantially parallel planes, the wedge body 40 at face 44 must have a diameter greater than that of the gap 70 such that the upper and lower members 22,24 become urged apart when the first and second inclined surfaces 42a,42b are wedged against respective interior surfaces 22b,24b of the upper and lower members 22,24.

Concurrently with restoring the angle of lordosis, the wedge body 40 also deploys a plurality of spines 50, which serve to secure the cage component 20 to the vertebral body end plates P by means of an engaging tooth 52 which is adapted to penetrate the end plate P. Preferably each upper and lower member 22,24 defines a through passage 26 confined by the plate to carve out one or more spines 50. Thus, each spine 50 has a free end 54 and a depending end 56. Again, as previously noted, a plate lends itself to the creation of such plurality of spines 50 by simple machining techniques. Thus, each spine 50 is integrally formed to depend from either an upper member 22 or a lower member 24. Each spine 50 has at lease one tooth 52 facing outwardly at the free end 54, the tooth preferably forming a penetrating tip or spike.

Each spine 50 is further bent inward towards gap 70 to dispose the tip of tooth 52 below the plane of its respective bearing surface 22a,24a. Necessarily then, the spine 50 on which the tooth 52 resides must depend into the gap 70, forming a desired protuberance which permits deployment of the spine 50 and associated tooth 52 by riding an inclined surface 42a,42b of wedge body 40 during its insertion. Obviously, the spine 50 and tooth 52 must be positioned such that each is in registry with its associated through passage 26 so that spine and tooth properly deploy without interference from an associated plate wall of the upper or lower member 22,24.

In order that the device 10 be easily surgically removed by reversing the wedge insertion procedure, an essential property of each spine 50 is a resilient memory that permits return of the spine 50 back to it original resting state (i.e. bent into the gap 70) when the wedge body 40 is removed. Again, choice of materials may include titanium, stainless steel or other surgical grade material which provides the spine 50 with resilience as a material property. The chosen material preferably both permits bending of the spine 50 into the gap 70 and tempering to create resilience of the spine 50.

The preferred configuration of the spines 50 relative to one another is understood by viewing FIG. 2, FIG. 5 and FIG. 6 together. By forming a sinuate through passage 26, a repetitive pattern including a first spine 50*a* and a second spine 50*b* is defined. Obviously, the number of spines so formed is a matter of preference. Each spine 50 is substantially perpendicular to the resilient web 60, and, substantially parallel with one another. Moreover, each depending end 54 of each of the spines 50*a*,50*b* is proximately opposed to each free end 54, thus defining an end-to-end relationship.

Therefore, the wedge body 40 preferably defines a recessed ramp 46 in an associated inclined surface 42*a*,42*b*. The ramp 46 receives the spine 50 which has its free end 54 farthest from web 60 and, hence, closest to the wedge body 40 when inserted from an anterior approach to the cage component 20.

For example, in the preferred embodiment as shown in FIG. 2, the ramp 46 aligns with the second spine 50*b* when the wedge body 40 is housed in the gap 70. Thus, as can be best understood and viewed in FIG. 7, when face 44 passes into gap 70, the first inclined surface 42*a* drives up first spine 50*a* at approximately the same rate as ramp 46 drives up second spine 50*b*. Therefore, when wedge body 40 is fully inserted and housed within gap 70, both the free end 54 of second spine 50*b* as well as the free end 54 of first spine 50*a* rests upon inclined surface 42*a* of wedge body 40, thus presenting a coplanar relationship. Because interior surfaces 22*b*,24*b* of upper and lower members 22,24 are nesting contiguously against inclined surfaces 42*a*,42*b*, respectively, each tooth 52 is fully deployed beyond an associated bearing surface 22*a*,24*a*.

Considering now the contraction mechanism 30 of the preferred embodiment, an assembly of coacting parts are shown for drawing the wedge body 40 into a nesting relationship within the cage component 20. Such assembly includes a lobe 32 depending from either one of the members 22,24, and chosen to be shown in FIG. 2 as depending from the interior surface 24*b* of lower member 24 into the gap 70. The lobe 32 has a threaded aperture 34 defining threads 35, the lobe 32 serving as an anchor point against which a pulling force may act to draw the wedge body 40 toward the cage component 20.

To provide such a coacting force, a threaded shaft 80 passes through the wedge body 40 and the lobe 32, the shaft 80 both having a matingly threaded portion 82 received by the threaded aperture 34 of the lobe 32, and, a head portion 84 rotatably seated in the wedge body 40. The head portion 84 includes a socket 88 adapted to receive a conventional driver tool T (FIG. 1), for turning the shaft 80.

To accommodate the shaft 80, wedge body 40 defines a tunnel 36 (best seen in FIG. 4). However, the wedge body includes a threadless seat 38 for receiving the head portion 84. This seat 38 permits free rotation of the head portion 84 within the wedge body 40 and therefore permits the threaded portion 82 to advance the wedge body 40 towards the cage component 20 as the shaft 80 is turned while the threaded portion 82 is engaged to lobe 32. Thus, the threaded portion 82 must have a predetermined length sufficient to extend proximate the front face 44 of the wedge body 40 to coact with the lobe 32. A simpler wedge body 40 may be seen in FIG. 3, which omits the seat 38 and includes only a tunnel 36, thus permitting the head portion 84 to protrude from face 48, rather than being flush with face 48. Regardless of choice of embodiment of the wedge body, the principles of coactive operation of the wedge body 40, cage component 20 and contraction mechanism 30 are unaffected.

To allow the wedge body 42 to be fully housed in the gap 70, the front face 44 must not interfere with lobe 32. Therefore, a cavity 49 is defined by the wedge body 40 which receives the lobe 32. As can be appreciated from FIG. 7, the cavity 49 is approximately as deep as the length of the inclined surfaces 42*a*,42*b*, leaving a septal portion 62 of wedge body 40 of sufficient thickness to permit the threadless seat 38 to be defined in rear face 48. Thus, when the head portion 84 of the shaft 80 is rotatably seated within the seat 38, the threaded portion 82 resides fully within cavity 49 and extends proximately toward face 44, having a predetermined length sufficient to engage the lobe 32. However, since the wedge body 40 is sized and dimensioned to approximate the size and dimensions of the gap 70, the shaft 80 should not significantly extend beyond the front face 44 of the wedge body 40. Otherwise, by having an excessively long shaft 30, the terminal end of the threaded portion 82 would eventually abut against web 60, thereby hindering complete insertion of the wedge body 40 into gap 70. However, as may be adapted by one of ordinary skill in the art, the coacting contraction means 30 described above may be altered to accomplish the intended purposes described herein without deviating from the scope of the claimed invention and its described purposes, and, other adequate embodiments of the contraction means 30 are therefore anticipated by the exemplary version described.

Figure 8:
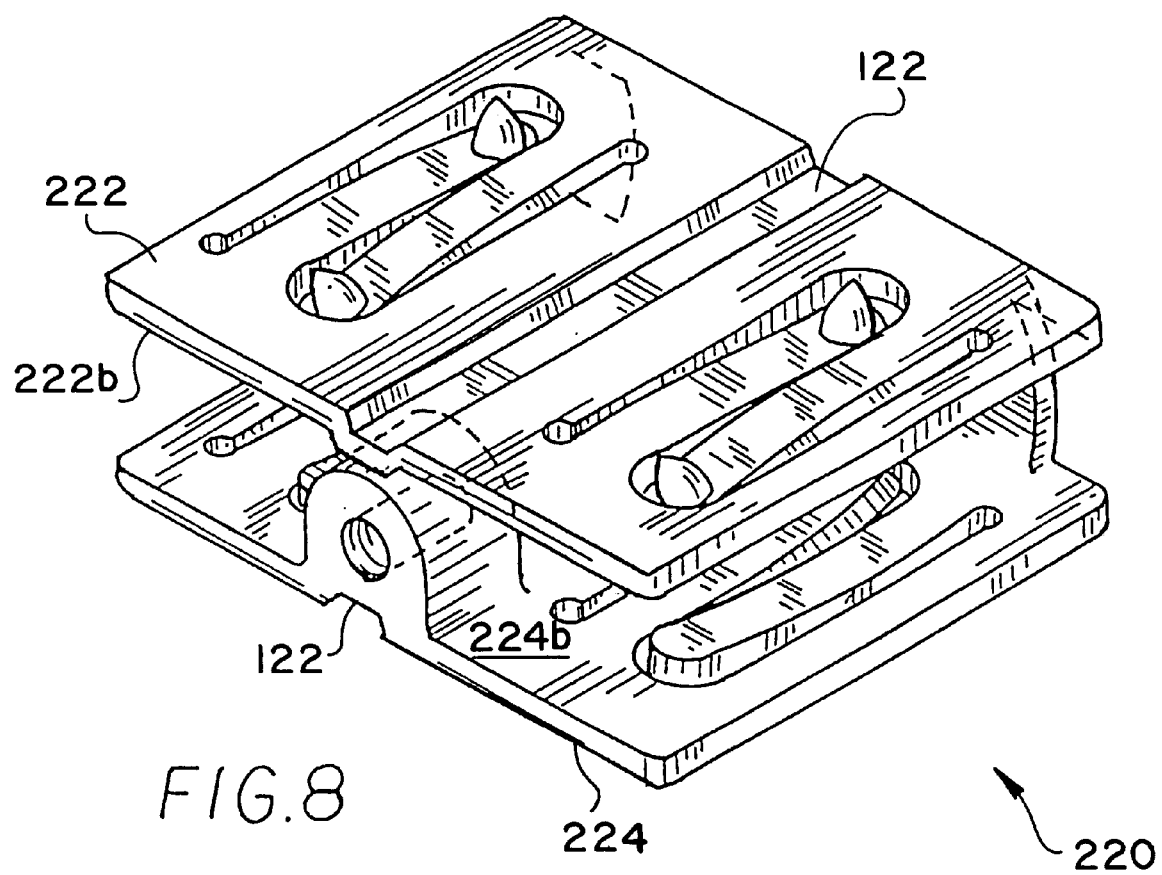
FIG. 8 is a second embodiment of the cage component of the intervertebral body fusion device.

Additional embodiments of the cage component 20 may be envisioned as well which operate upon the same principles and employ the same essential structural features described herein. For example, FIG. 8 describes a cage component 220 identical in all respects to the embodiment of cage component 20, excepting an additional track 122 which is defined on the interior surfaces 222*b*,224*b* in upper and lower members 222,224, respectively. Although not shown, a wedge body essentially identical to that of wedge body 40 has a mating groove for receiving the track 122. The groove and track arrangement may be helpful in guiding the wedge and cage components into proper nesting relationship.

Figure 9:
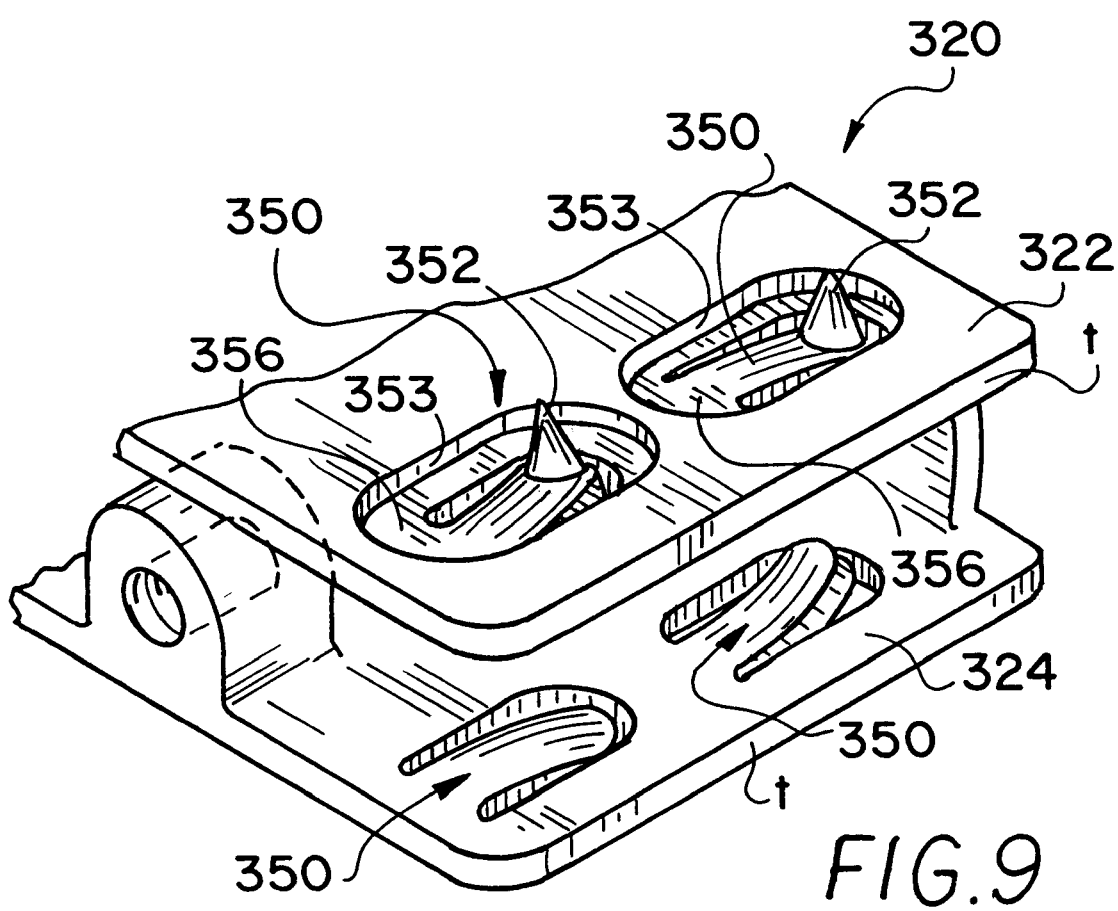
FIG. 9 is a third embodiment of the cage component of the intervertebral body fusion device.

Likewise, FIG. 9 represents yet another embodiment of the cage component, 320, wherein the spines 350 are also machined out of a plate of upper and lower members 322,324, however, into a configuration different from that of the preferred configuration. Moreover, each spine 50 has a tooth 352 which is machined from the thickness, t, of the plate, although shown in exaggerated size for clarity of illustration. This allows the tooth 352 to be integrally formed from a plate comprising upper or lower member 322,324. A resulting shoulder 352 and bed 356 is thus formed, with each spine 350 being defined in the same plane as bed 356. Each spine 350 may be bent inward at rest, with a resulting outward bend after insertion of a wedge body. The wedge body must however be adapted with a knob (not shown) or ramp protruding outward from an inclined surface to drive the spines 350 outward.

Finally, referring back to FIG. 1, in its final surgically-implanted position, the wedge body 40 of the various embodiments can be understood to be substantially fully drawn within the cage component 20, resulting in a full deployment of teeth 52 and associated spines 50 into the adjacent end plates P of the vertebral bodies B, thereby simultaneously restoring the angle of lordosis to the spine L.

It is to be understood that the present invention is not limited to the embodiments described above, but encompasses any and all embodiments within the scope of the following claims.

I claim:

1. An intervertebral body fusion device comprising:
 a cage component including a rigid upper member defining a bearing surface, an opposing interior surface and a through passage confined by said upper member;

a rigid lower member defining a bearing surface, an opposing interior surface, and a through passage confined by said lower member;

a resilient web bridging said upper member and said lower member and defining a living hinge, said web spacing said members from one another thereby defining a gap of a predetermined distance for receiving a wedge body between said members;

a first spine having a free end and a depending end, said first spine having a tooth, said depending end depending from said upper member and disposing said tooth below said bearing surface, and said first spine further positioning said tooth in registry with said through passage of said upper member;

a wedge body dimensioned and configured to be received and substantially housed in said gap, said wedge body having a predetermined diameter greater than the predetermined distance of said gap, whereby said upper and lower members become urged apart when said wedge body is inserted into said gap; and a contraction means for drawing said wedge body into said gap so as to nest within said cage component.

2. The intervertebral body fusion device according to claim 1 wherein said wedge body defines a first inclined surface and an opposing second inclined surface defining a predetermined fixed angle relative to each other.

3. The intervertebral body fusion device according to claim 2 wherein said upper member further defines a second through passage confined by said upper member; and further includes a second spine having a free end and a depending end, said second spine having a tooth, said depending end depending from said upper member and disposing said tooth in said gap proximate said interior surface of said upper member, and said second spine further positioning said tooth in registry with said second through passage of said upper member; and wherein further said wedge body defines a recessed ramp in said first inclined surface, said ramp aligning with said second spine when said wedge body is housed in said gap.

4. The intervertebral body fusion device according to claim 3, wherein said first and second spines are substantially perpendicular to said flexible web, and, said depending end of each of said first and second spines are proximately opposed to each said free end.

5. The intervertebral body fusion device according to claim 3, wherein said lower member further defines a through passage confined by said lower member; and further includes a spine having a free end and a depending end, said spine having a tooth, said depending end depending from said lower member and disposing said tooth in said gap proximate said interior surface of said lower member, and said spine further positioning said tooth in registry with said through passage of said lower member; and wherein further said wedge body defines a recessed ramp in said second inclined surface, said ramp aligning with said spine of said lower member when said wedge body is housed in said gap.

6. The intervertebral body fusion device according to claim 1, wherein said upper member and said lower member each define a plate.

7. The intervertebral body fusion device according to claim 6, wherein said spine is integrally formed in said plate and substantially residing in said through passage when formed, said spine and plate being constructed of a flexible material permitting bending of said spine into said gap and tempering of said material to create resilience of said spine.

8. The intervertebral body fusion device according to claim 1, wherein said cage component, wedge body and contraction means are manufactured from a surgical grade material selected from the group consisting of titanium and stainless steel.

9. The intervertebral body fusion device according to claim 1, wherein the contraction means is an assembly further comprising a lobe depending from one of said upper or lower members, said lobe having a threaded aperture; and a shaft passing through said wedge body and said lobe, said shaft having threaded portion received by said threaded aperture and a head portion rotatably seated in said wedge body, said wedge body including a threadless seat for receiving said head portion and permitting free rotation of said head portion within said wedge body, and, said threaded portion having a predetermined length between said wedge body and said lobe when said threaded portion is engaged.

10. The intervertebral body fusion device according to claim 9, wherein said head portion includes a socket adapted to receive a driver tool for turning said shaft.

11. An intervertebral body fusion device comprising:

a cage component including a rigid upper member defining a bearing surface, an opposing interior surface and a through passage confined by said upper member;

a rigid lower member defining a bearing surface, an opposing interior surface, and a through passage confined by said lower member, said lower member attached to said upper member and disposed apart to define a gap of a predetermined distance for receiving a wedge body between said members;

a first spine having a tooth, said first spine depending from said upper member and disposing said tooth within said gap proximate said interior surface of said upper member, and further positioning said tooth in registry with said through passage of said upper member;

a wedge body defining a first inclined surface and an opposing second inclined surface defining a predetermined fixed angle relative to each other, said wedge body dimensioned and configured to be received and substantially housed in said gap, said wedge body having a predetermined diameter greater than the predetermined distance of said gap such that said upper and lower members become urged apart when said first and second inclined surfaces wedge against respective interior surfaces of said upper and lower members; and a contraction means for drawing said wedge body into said gap so as to nest within said cage component;

whereby, when said wedge body engages said spine upon insertion into said gap, said wedge body deploys said spine and said tooth by driving said tooth through said through passage.

12. The intervertebral body fusion device according to claim 11, further comprising a resilient web bridging said upper member and said lower member and defining a living hinge, said web spacing said members from one another thereby defining said gap.

13. The intervertebral body fusion device according to claim 11 wherein said upper member further defines a second through passage confined by said upper member; and further includes a second spine having a free end and a depending end, said second spine having a tooth, said depending end depending from said upper member and disposing said tooth in said gap proximate said interior surface of said upper member, and said second spine further positioning said tooth in registry with said second through passage of said upper member; and wherein further said wedge body defines a recessed ramp in said first inclined surface, said ramp aligning with said second spine when said wedge body is housed in said gap.

14. The intervertebral body fusion device according to claim 13, wherein said first and second spines are substantially perpendicular to said flexible web, and, said depending end of each of said first and second spines are proximately opposed to each said free end.

15. The intervertebral body fusion device according to claim 13, wherein said lower member further defines a through passage confined by said lower member; and further includes a spine having a free end and a depending end, said spine having a tooth, said depending end depending from said lower member and disposing said tooth in said gap proximate said interior surface of said lower member, and said spine further positioning said tooth in registry with said through passage of said lower member; and wherein further said wedge body defines a recessed ramp in said second inclined surface, said ramp aligning with said spine of said lower member when said wedge body is housed in said gap.

16. The intervertebral body fusion device according to claim 11, wherein said upper member and said lower member each defines a plate.

17. The intervertebral body fusion device according to claim 16, wherein said spine is integrally formed in said plate and substantially residing in said through passage when formed, said spine and plate being constructed of a flexible material permitting bending of said spine into said gap and tempering of said material to create resilience of said spine.

18. The intervertebral body fusion device according to claim 11, wherein said cage component, wedge body and contraction means are manufactured from a surgical grade material selected from the group consisting of titanium and stainless steel.

19. The intervertebral body fusion device according to claim 11, wherein the contraction means is an assembly further comprising a lobe depending from one of said upper or lower members, said lobe having a threaded aperture; and a shaft passing through said wedge body and said lobe, said shaft having threaded portion received by said threaded aperture and a head portion rotatably seated in said wedge body, said wedge body including a threadless seat for receiving said head portion and permitting free rotation of said head portion within said wedge body, and, said threaded portion having a predetermined length between said wedge body and said lobe when said threaded portion is engaged.

20. The intervertebral body fusion device according to claim 19, wherein said head portion includes a socket adapted to receive a driver tool for turning said shaft.

* * * * *